United States Patent [19]

Koch et al.

[11] Patent Number: 4,483,961
[45] Date of Patent: Nov. 20, 1984

[54] POLYMERIC CYCLOPENTADIENE DERIVATIVES, METHOD FOR PREPARING AND USE THEREOF

[75] Inventors: Diether Koch, Mettmann, Fed. Rep. of Germany; Bruce A. Gruber, Worthington, Ohio; Heimo J. Langer; William R. Dunnavant, both of Columbus, Ohio

[73] Assignee: Ashland Oil, Inc., Ashland, Ky.

[21] Appl. No.: 524,050

[22] Filed: Aug. 17, 1983

Related U.S. Application Data

[63] Continuation-in-part of Ser. No. 300,786, Sep. 10, 1981, Pat. No. 4,412,088.

[51] Int. Cl.$^3$ ............................................. C08L 61/00
[52] U.S. Cl. .................................. 524/542; 523/139; 523/144; 523/466; 524/593; 524/877; 528/220; 528/246
[58] Field of Search .................. 523/139, 144, 466; 524/849, 542, 877, 593; 585/23; 528/226, 246

[56] References Cited

U.S. PATENT DOCUMENTS

| | | | |
|---|---|---|---|
| 2,589,969 | 3/1952 | Schutze et al. | 585/357 |
| 3,051,765 | 8/1962 | McCain | 585/357 |
| 3,192,275 | 6/1965 | Freiesleben | 585/357 |
| 3,262,990 | 7/1966 | Horwitz et al. | |
| 3,376,304 | 4/1968 | Mahrbacher et al. | 585/23 |
| 3,390,156 | 6/1968 | Hurwitz et al. | 585/23 |
| 4,246,167 | 1/1981 | Grimm et al. | 523/144 |
| 4,320,218 | 3/1982 | Gruber et al. | 260/998.18 |

FOREIGN PATENT DOCUMENTS 635353 3/1983 Switzerland .

OTHER PUBLICATIONS

McCain, J. Org. Chem., 23, 632, (1958).
Angus et al., J. Chem. Soc., 1409, (1960).
Neuenschwander et al., Helv. Chim. Acta, 46, 1760, (1963).
Meuche et al., Helv. Chim. Acta, 47, 1211, (1964).
Neuenschwander et al., Chimia, 35, 476, (1981).

*Primary Examiner*—Allan M. Lieberman
*Attorney, Agent, or Firm*—Pollock, Vande Sande & Priddy

[57] ABSTRACT

Polymeric cyclopentadiene derivatives, method for preparing polymeric cyclopentadiene derivatives, and use of polymeric cyclopentadiene derivatives in curable binder compositions.

36 Claims, No Drawings

POLYMERIC CYCLOPENTADIENE DERIVATIVES, METHOD FOR PREPARING AND USE THEREOF

CROSS REFERENCE TO RELATED APPLICATION

This application is a continuation-in-part of our copending U.S. patent application Ser. No. 300,786 filed on Sept. 10, 1981 and entitled "Cyclopentadiene Derivatives, Method for Preparing and Use Thereof" and now U.S. Pat. No. 4,412,088.

DESCRIPTION

1. Technical Field

The present invention is directed to new polymeric cyclopentadiene derivatives which are particularly useful in binder compositions. Such compositions are curable at normal room temperatures. The compositions are capable of being cured at normal room temperatures by a gaseous curing agent or an acidic catalyst incorporated into the binder. The compositions of the present invention are especially useful as foundry binders. The present invention is also directed to a method for preparing certain polymeric derivatives of cyclopentadiene.

2. Background Art

In the foundry art, cores and molds used in making metal castings are generally prepared from shaped, cured mixtures of aggregate material (e.g., sand) and a binder. One of the preferred techniques of making these sand cores includes the basic steps of mixing the sand with a resin binder and a curing catalyst, molding the mixture to the desired shape and allowing it to cure and solidify at room temperature without the application of heat. Resins useful in this technique include furfuryl alcohol-formaldehyde polymers, furfuryl alcohol-urea-formaldehyde polymers, alkyd isocyanate resins, and sodium silicate binders. Such technique is commonly referred to as a "no bake" process.

Another technique employed includes the basic steps of mixing the aggregate with a resin binder, molding the mixture to the desired shape, and curing the shape by passing a gaseous catalyst through it. This technique is often referred to as the "cold box" method. Binders which are suitable for use in such processes must possess a number of important characteristics. For instance, the binders must be capable of providing relatively high strength characteristics to the molded article and must be capable of curing to a considerable degree at normal room temperatures. Also, since curing of the binders occurs while as a thin layer of film on the aggregate and the aggregate can act as a heat sink, the curing does not necessarily proceed in the same manner as when the binder is cured in bulk. In addition, foundry cores and molds must retain the strength properties until the metal solidifies in the mold, but must lose such properties due to their exposure at higher temperatures so that after solidification of the metal, the cores or molds can readily be broken down for shake-out or removal from the casting. Accordingly, providing new binders for foundry applications which contain the necessary properties is quite difficult. This problem is made more acute when the object is a relatively inexpensive binder.

It has also been discovered that fulvenes and/or fulvene prepolymers could be employed as binders for foundry applications as described in U.S. Pat. No. 4,246,167 entitled "Foundry Binder Composition" to Grimm, et al., and assigned to Ashland Oil Inc., the assignee of the present application. However, the use of such fulvenes has not been entirely satisfactory since such are somewhat susceptible to degradation from atmospheric oxygen and have an unpleasant odor.

In addition, applicants in copending application Ser. No. 300,786 disclose certain derivatives of cyclopentadiene and/or of methyl cyclopentadiene which have improved resistance to atmospheric oxygen, and reduced odor as compared to the fulvenes discussed hereinabove.

DISCLOSURE OF INVENTION

The present invention provides a process for preparing certain polymeric derivatives of cyclopentadiene and/or of methyl substituted cyclopentadiene. The present invention is also concerned with novel polymeric derivatives of cyclopentadiene and/or of methyl substituted cyclopentadiene which can be produced by the process of the present invention. The present invention is also concerned with the use of certain polymeric derivatives of cyclopentadiene and/or of methyl substituted cyclopentadiene in binder compositions and especially foundry binder compositions.

The polymers of the present invention have reduced odor as compared to the fulvenes and the cyclopentadiene derivatives discussed hereinabove. Moreover, the polymers of the present invention, when used as in a binder composition for molded articles, demonstrate greater erosion resistance when compared to the use of the fulvenes and the cyclopentadiene derivatives discussed hereinabove.

The present invention is concerned with polymeric cyclopentadiene derivatives having recurring units of the formula I or isomers thereof or mixtures thereof:

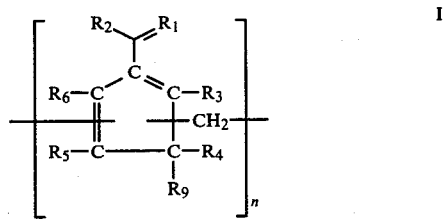

Each $R_1$ and $R_2$ individually is preferably a hydrocarbon containing 1 to 10 carbon atoms, or a hydrocarbon containing one or more oxygen bridges, or a furyl group; or are interconnected and together with the carbon atom to which they are connected from a cycloaliphatic hydrocarbon group, or one of $R_1$ or $R_2$ is hydrogen. Each $R_3$, $R_4$, $R_5$, $R_6$, and $R_9$ individually is hydrogen or methyl or —$CH_2$— or

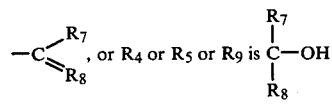

provided that at least two (2) of $R_3$, $R_4$, $R_5$, $R_6$, and $R_9$ are hydrogen. It is further provided that at least two of said $R_3$, $R_5$, $R_6$, and $R_4$ or $R_9$ are —$CH_2$—. When $R_4$ is —$CH_2$—, then $R_9$ is other than —$CH_2$— and vice versa. Each $R_7$ and $R_8$ individually is a hydrocarbon group containing 1–10 carbon atoms or a hydrocarbon group containing one or more oxygen bridges in the chain and containing up to 10 carbon atoms, or are interconnected and together with the carbon atom to which they are connected, form a cycloaliphatic hydrocarbon group, or furyl, or one of $R_7$ or $R_8$ is hydrogen. In addition, n is an integer of at least 2.

The present invention is also concerned with a curable composition which includes at least one polymeric cyclopentadiene derivative of the type discussed hereinabove, and an acidic catalyst. The acidic catalyst has a pKa of about 4 or less. The acidic catalyst is incorporated into the composition prior to molding or is provided by passing a gas through the molded composition.

The present invention is also concerned with molding compositions which include a major amount of aggregate and an effective bonding amount up to about 40% by weight of the aggregate of the above-defined curable composition.

The present invention is also directed to a process for the fabrication of molded articles which includes the following steps:

(a) mixing aggregate with a bonding amount up to about 40% by weight based upon the weight of the aggregate of a binder composition of the type described hereinabove which contains the acidic catalyst;

(b) introducing the composition obtained from step (a) into a pattern;

(c) hardening the composition in the pattern to become self-supporting; and (d) thereafter removing the shaped article of step (c) from the pattern and allowing it to further cure, thereby obtaining a hardened, solid, cured, molded article.

The present invention is also concerned with a process for the fabrication of molded articles which comprises:

(a) mixing the aggregate with a bonding amount up to about 40% by weight based upon the weight of the aggregate of a polymeric cyclopentadiene derivative of the type discussed hereinabove;

(b) introducing the composition obtained from step (a) into a pattern;

(c) hardening the composition in the pattern to become self-supporting by passing an acidic gas through the composition; and (d) thereafter removing the shaped article of step (c) from the pattern and allowing it to further cure, thereby obtaining a hardened, solid, cured, molded article.

The present invention is also concerned with a process for casting a metal which includes fabricating a shape as described hereinabove, pouring metal while in the liquid state into or around the shape, allowing the metal to cool and solidify, and then separating the molded metal article.

The present invention is also concerned with a process for preparing polymeric cyclopentadiene derivative which comprises reacting cyclopentadiene derivative having the formula:

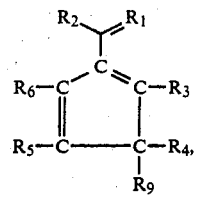

isomers, or mixtures thereof; wherein each $R_1$ and $R_2$ individually is a hydrocarbon containing 1 to 10 carbon atoms or a hydrocarbon containing one or more oxygen bridges in the chain and contains up to 10 carbon atoms; or are interconnected and together with the carbon atom to which they are connected, form a cycloaliphatic hydrocarbon group or one or $R_1$ or $R_2$ is hydrogen; each $R_3$, $R_4$, $R_5$, $R_6$, and $R_9$ individually is hydrogen, methyl, or

or $R_4$ or $R_9$ or $R_5$ is

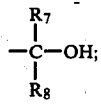

wherein each $R_7$ and $R_8$ individually is a hydrocarbon containing 1 to 10 carbon atoms or a hydrocarbon containing one or more oxygen bridges in the chain and containing up to 10 carbon atoms; or are interconnected and together with the carbon atom to which they are connected form a cycloaliphatic hydrocarbon group or furyl or one of $R_7$ or $R_8$ is hydrogen, and provided that at least four of $R_3$, $R_4$, $R_5$, $R_6$, and $R_9$ are hydrogen; with formaldehyde in the presence of a basic catalyst to provide a polymeric cyclopentadiene derivative.

Moreover, the present invention is directed to polymeric cyclopentadiene derivatives obtained by the process described hereinabove.

BEST AND VARIOUS MODES FOR CARRYING OUT THE INVENTION

The polymeric cyclopentadiene derivatives of the present invention are represented by the recurring formula I below or isomers or mixtures thereof:

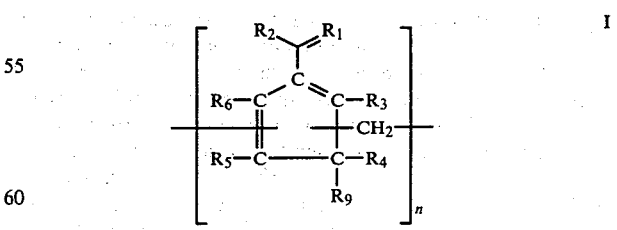

Each $R_1$ and $R_2$ individually is a hydrocarbon group containing 1 to 10 carbon atoms such as an alkyl, aryl, alkaryl, or aralkyl group; or a furyl group; or are interconnected and together with the carbon atom to which they are connected, form a cycloaliphatic hydrocarbon group or a hydrocarbon group containing one or more oxygen bridges in the chain containing up to 10 carbon atoms; or one of $R_1$ or $R_2$ is hydrogen.

The hydrocarbon groups can be free from non-benzenoid unsaturation or can include ethylenic unsaturation. Examples of some hydrocarbon groups include alkyl groups, such as methyl, ethyl, propyl, amyl and butyl; aryl groups, such as phenyl and naphthyl; alkaryl groups, such as benzyl; aralkyl groups; and ethylenically unsaturated groups, such as vinyl. Examples of some cyclic groups include cycloaliphatic groups, such as cyclopentyl, cyclohexyl, and cycloheptyl.

Preferably at least one of $R_1$ and $R_2$ is methyl and the other is an alkyl of 2 to 5 carbon atoms.

Each $R_3$, $R_4$, $R_5$, $R_6$, and $R_9$ individually is hydrogen or methyl or

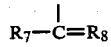

or $R_4$ or $R_5$ or $R_9$ is:

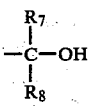

At least two of $R_3$, $R_4$, $R_5$, $R_6$, and $R_9$ are hydrogen. At least two of said $R_3$, $R_5$, $R_6$, and $R_4$ or $R_9$ are —$CH_2$—. Each $R_7$ and $R_8$ individually is a hydrocarbon group containing 1 to 10 carbon atoms, or a hydrocarbon group containing one or more oxygen bridges in the chain containing up to 10 carbon atoms, or are interconnected and together with the carbon atom to which they are connected form a cycloaliphatic hydrocarbon group, or furyl, or one of $R_7$ or $R_8$ is hydrogen. Preferably, at least one of $R_7$ and $R_8$ differs from $R_1$ and $R_2$. The preferred $R_7$ and $R_8$ groups are alkyl, more preferably at least one $R_7$ and $R_8$ is methyl. When a

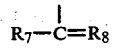

group is present, such is preferably at the $R_4$ or $R_5$ or $R_9$ position.

In addition, if excess aldehyde or ketone is employed in the preparation of the monomeric cyclopentadiene derivatives, such could contain compounds wherein $R_4$ or $R_9$ or $R_5$ can have the structure:

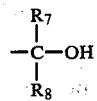

In such a case, $R_3$ and $R_6$ will be as previously described.

An example of an isomer of formula I above can be represented by the structure:

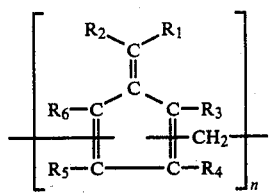

Examples of some cyclopentadiene derivatives from which the polymeric cyclopentadiene derivatives of the present invention can be obtained include fulvenes such as methylisobutylfulvene ($R_1$ is methyl; $R_2$ is isobutyl; $R_3$, $R_4$, $R_5$, and $R_6$ are H); cyclohexylfulvene ($R_1$ and $R_2$ are interconnected and form a cyclohexyl ring with the common carbon atom to which they are connected; $R_3$, $R_4$, $R_5$, and $R_6$ are H); methylethylfulvene ($R_1$ is methyl; $R_2$ is ethyl; $R_3$, $R_4$, $R_5$, and $R_6$ are H); diphenylfulvene ($R_1$ and $R_2$ are phenyl; $R_3$, $R_4$, $R_5$, and $R_6$ are H); furylfulvene ($R_1$ is furyl; $R_2$ is H; and $R_3$, $R_4$, $R_5$, and $R_6$ are H); diisobutylfulvene ($R_1$ and $R_2$ are isobutyl; $R_3$, $R_4$, $R_5$, and $R_6$ are H); isophorone fulvene ($R_1$ and $R_2$ are interconnected and form an isophorone ring with the common carbon atom to which they are connected; $R_3$, $R_4$, $R_5$, and $R_6$ are H).

Fulvenes have been known for many years as well as their method of preparation. Also, it has been known that fulvenes polymerize in the presence of acids.

Suggestions of methods for preparing fulvenes can be found in U.S. Pat. Nos. 2,589,969; 3,051,765; and 3,192,275. In addition, fulvenes can be purified by distillation according to a method by Kice, J.A.C.S. 80, 3792 (1958), and the method of McCaine, J. Chem. Society 23, 632 (1958).

The polymeric cyclopentadiene derivatives of the present invention can be prepared by reacting a fulvene of the formula:

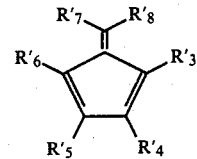

wherein each $R'_7$ and $R'_8$ is the same as $R_7$ and $R_8$ respectively as defined hereinabove. Each $R'_3$, $R'_4$, $R'_5$, and $R'_6$ individually is hydrogen or methyl provided that a maximum of only one such $R'_3$, $R'_4$, $R'_5$, and $R'_6$ is methyl, and, in addition, if excess aldehyde or ketone is employed in the preparation of the fulvene, $R'_4$ or $R'_5$ can have the structure:

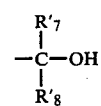

In such a case, $R_3$ and $R_6$ will be as previously discussed.

The fulvene can be prepared by reacting cyclopentadiene and/or methylcyclopentadiene with a carbonyl compound from the group of aldehyde or ketone in the presence of a basic catalyst. The preferred carbonyl compounds have 1 to 8 carbon atoms and more preferably, are ketones having a hydrogen on the alpha carbon atom, and most preferably, are ketones with at least one methyl group. The reaction is generally carried out at temperatures of about 40°–90° C. and preferably, at about 50°–80° C. Examples of some basic catalysts include: strong bases (e.g. KOH), an amine, and basic ion exchange resins. Suggestions of methods for preparing fulvenes can be found in U.S. Pat. Nos. 2,589,969; 3,051,765; and 3,192,276. Suggestions of preparing fulvene polymers can be found in U.S. Pat. Nos. 2,512,698; 2,587,791; 2,898,325; and 3,390,156. The amount of catalyst employed is usually about 20 to about 50 mole percent based on the moles of cyclopentadiene or methylcyclopentadiene used.

About stoichiometric amounts (e.g.-a maximum of about a 10% excess of either reactant) is usually employed. The reaction is preferably carried out in an alcoholic solution. The reaction usually takes about 0.5 to about 3 hours. The amount of diluent (e.g. alcohols such as methanol, ethanol, isopropanol, n-propanol, butanols, and amyl alcohol) is usually about 50 to about 150 ml per mole of cyclopentadiene or methylcyclopentadiene. The preferred alcohols employed have three or more carbon atoms. Most preferably a mixture of methanol with such higher alcohols having three or more carbon atoms is employed.

Polymeric derivatives within the scope of the present invention can be prepared by either of the following two procedures:

1. The reaction product from the above discussed type of reaction (i.e.-the fulvene) is reacted with formaldehyde as will be discussed herein below to provide the polymers of the present invention.

2. The reaction product from the above discussed type of reaction (i.e.-the fulvene) is reacted with a carbonyl compound in general (e.g.-acetone,methylethylketone and methylisobutyl ketone) to provide a disubstituted cyclopentadiene of the type disclosed in application 300,786, disclosure of which is incorporated herein by reference. This reaction is also carried out in the presence of a basic catalyst of the type and amounts discussed hereinabove employed to prepare the fulvenes.

The preferred carbonyl compounds contain 1–8 carbon atoms and preferably are ketones containing at least one methyl group. The most preferred ketone is acetone.

This reaction is generally carried out at temperatures of about 40°–90° C. and preferably at about 60°–80° C. About stoichiometric amounts (e.g.-about a maximum of a 10% excess of either reactant) are usually employed. However, when acetone is used as the only carbonyl compound in both stages of the process, at least about 2 times the stoichiometric amount (i.e. 4 moles per mole of cyclopentadiene or methylcyclopentadiene) of acetone is preferably employed. And more preferred at least about 3 times, and most preferred about 3 to about 5 times the stoichiometric amount is employed. This reaction is preferably carried out in an alcoholic solution. The reaction usually takes about 5 to about 24 hours. The amounts of catalyst and diluent are usually within the same range as those amounts employed in preparing the fulvene.

By following the above process, a mixture containing about 30–60% of disubstituted cyclopentadiene derivatives of the type disclosed in said application, 300,786 can be obtained.

The reaction products containing the disubstituted cyclopentadiene derivatives is reacted with formaldehyde as will be discussed herein below to provide the polymers of the present invention.

Mixtures of any of the above fulvenes and/or disubstituted cyclopentadiene derivatives can be employed, if desired.

The fulvene and/or disubstituted cyclopentadiene derivative is then reacted with formaldehyde to provide the polymeric derivatives of the present invention. Generally about 0.1 to about 1 moles of formaldehyde and preferably about 0.25 to about 0.75 moles of formaldehyde are employed for each mole of cyclopentadiene type reactant.

The formaldehyde employed is preferably in the form of a methanol solution. However, other forms capable of supplying formaldehyde to the reaction mass such as paraformaldehyde and trioxane can be employed.

Paraformaldehyde is a substantially water-free source of formaldehyde and is a mixture of polyoxymethylene glycol which usually contains from about 90 to about 99% by weight of formaldehyde with the balance consisting principally of free and combined water. It is recognized, of course, that paraformaldehyde can include mixtures of polyoxymethylene glycols containing down to about 80% formaldehyde with the balance consisting principally of free and combined water, as long as the mixture is still a solid material. Usually, commercial grades of paraformaldehyde contain from about 91 to about 98% formaldehyde. The chemical composition of paraformaldehyde can be expressed by the following formula:

wherein n is equal to 8 to 100. Normally, the majority of the polyoxymethylene glycols in paraformaldehyde contain over about 12 formaldehyde units per molecule. Paraformaldehyde has a melting point of from about 120° to about 170° C.

This reaction is also carried out in the presence of a basic catalyst of the type and amounts discussed hereinabove employed to prepare the fulvenes.

This reaction is generally carried out at temperatures of about 60°–90° C. and preferably at about 60°–80° C. This reaction is preferably carried out in an alcoholic solution. The reaction usually takes about 5 to about 24 hours. The amounts of catalyst and diluent are usually within the same range as those amounts employed in preparing the fulvene.

By following the above procedures, the polymeric derivatives of the present invention are obtained. The polymeric derivatives preferably have molecular weights of about 350 to about 1525, and preferably n in formula I is an integer of about 2 to about 9.

Furthermore, the polymers can be reacted with ketones and preferably acetone in the presence of a basic catalyst under the same conditions as described hereinabove for the reaction of the fulvenes with the carbonyl compound to provide the disubstituted cyclopentadiene derivatives.

The polymers preferably are fluid enough so that when applied either per se or in admixture with the diluents will flow to coat the aggregate used.

The polymeric cyclopentadiene derivatives of the present invention are especially useful in binder compositions and particularly foundry binder composition. Mixtures of the polymeric cyclopentadiene derivatives can be used.

In addition, the binder composition of the present invention contains an acidic catalyst. The acidic catalysts employed have a pKa value of about 4 or less and include organic acids such as formic acid, oxalic acid, and the organic substituted sulfonic acids such as benzenesulfonic acid and toluenesulfonic acid, and preferably Lewis acids such as BF₃. The acidic catalyst can be provided in the foundry mix before molding (e.g.—"no bake" process), and/or by passing a gas through the molded composition such as an acid per se or a gas such as SO₂ which in conjunction with a component of the molded composition (e.g. a peroxide) forms an acid in situ.

The acidic catalyst when already in the mix prior to molding is generally present in amounts up to a maximum of about 5% by weight based upon the amount of binder employed. The minimum amount of acidic catalyst is usually about 0.8 percent based upon the amount of binder employed. When employing a "cold box" process usually up to about 5 seconds of gassing time is sufficient.

The polymeric cyclopentadiene derivatives can be employed in combination with fulvenes of the type discussed hereinabove, and/or with disubstituted cyclopentadiene derivatives and/or prepolymers thereof as discussed in U.S. Pat. Ser. No. 300,786, and/or with furfuryl alcohol and/or furan prepolymer foundry binder systems, and/or epoxy polymers and/or phenolic materials such as phenol, substituted phenols or phenolformaldehyde condensates.

The furan propolymers include reaction products of furfuryl alcohol and of aldehydes such as formaldehyde. In addition, the aldehyde-furfuryl alcohol reaction product can be modified with varying amounts of reactants such as urea. The mole ratios of formaldehyde to furfuryl alcohol which can be employed can vary widely. For instance, the furan polymer can be prepared from about 0.4 to about 4 moles of furfuryl alcohol per mole of formaldehyde, and preferably from about 0.5 to about 2 moles of furfuryl alcohol per mole of formaldehyde.

The furan polymer which can be employed in the present invention can be any of the various furan polymers which are known to be suitable for molding and especially foundry purposes. Examples of such furan polymers include those obtained from about 1 mole of urea, about 0.2 to 2 moles of furfuryl alcohol and about 1 to 3 moles of formaldehyde such as described in U.S. Pat. Nos. 3,222,315 and 3,247,556. Other suitable furan polymers are disclosed in U.S. Pat. No. 3,346,534. The furan polymers are usually prepared by polymerization in the presence of an acid catalyst. Usually when a furan polymer is employed, it is added together with furfuryl alcohol.

Examples of suitable epoxy polymers include epoxidized novolak polymers, glycidyl ethers of a polynuclear dihydric phenol, and reaction products thereof with polymers terminated with reactive groups. Preferably the epoxies employed are liquid. The preferred types of epoxy polymers are the polyepoxides of epichlorohydrin and bisphenol-A, i.e., 2,2-bis(p-hydroxyphenyl) propane. Other suitable epoxies as stated hereinabove include those obtained by reacting a polynuclear dihydric phenol with haloepoxy alkane in general.

Suitable polynuclear dihydric phenols can have the formula:

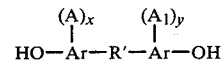

wherein Ar is an aromatic divalent hydrocarbon such as naphthalene and, preferably, phenylene, A and A₁ which can be the same or different are alkyl radicals, preferably having from 1 to 4 carbon atoms, halogen atoms, e.g., fluorine, chlorine, bromine and iodine, or alkoxy radicals, preferably having from 1 to 4 carbon atoms, x and y are integers having a value 0 to a maximum value corresponding to the number of hydrogen atoms on the aromatic radical (Ar) which can be replaced by substituents and R' is a bond between adjacent carbon atoms as in dihydroxydiphenyl or is a divalent radical including, for example:

$$-\underset{\underset{O}{\|}}{C}-,$$

—O—, —S—, —SO₂— and —S—S— and divalent hydrocarbon radicals, such as alkylene, alkylidene, cycloalipahtic, e.g., cycloalkylene, halogenated, alkoxy or aryloxy substituted alkylene, alkylidene and cycloalophatic radicals as well as aromatic radicals including halogenated, alkyl, alkoxy or aryloxy substituted aromatic radicals and a ring fused to an Ar group; or R' can be polyalkoxy, or polysiloxy, or two or more alkylidene radicals separated by an aromatic ring, a tertiary amino group, an ether linkage, a carbonyl group or a sulfur containing group such as sulfoxide, and the like.

Examples of specific dihydric polynuclear phenols include among others, the bis-(hydroxyphenyl) alkanes such as 2,2-bis-(4-hydroxyphenyl) propane, bis-(2-hydroxyphenyl) methane, bis-(4-hydroxyphenyl) methane, bis-(4-hydroxy-2,6-dimethyl-3-methoxyphenyl) methane, 1,1-bis-(4-hydroxyphenyl) ethane, 1,2-bis-(4-hydroxyphenyl) ethane, 1,1-bis(4-hydroxy-2-chlorophenyl) ethane, 1,1-bis-(3-methyl-4-hydroxyphenyl) propane, 2,2-bis-(3-phenyl-4-hydroxyphenyl) propane, 2,2-bis(2-isopropyl-5-hydroxyphenyl) propane, 2,2-bis(4-hydroxynaphthyl) pentane, bis-(4-hydroxyphenyl) phenylmethane, bis-(4-hydroxyphenyl) cyclohexylmethane, 1,2-bis-(4-hydroxyphenyl)-1-phenyl propane; di(hydroxyphenyl) sulfones such as bis(4-hydroxyphenyl) sulfone, 2,4' dihydroxydiphenyl sulfone, 5'-chloro-2,4'-dihydroxydiphenyl sulfone, and 5'-chloro-2,2'-dihydroxydiphenyl sulfone, and 5'-chloro-4,4'-dihydroxydiphenyl sulfone; di(hydroxyphenyl) ethers such as bis-(4-dihydroxy-phenyl) ether, the 4,3'-, 4,2'-, 2,2'-, 3,3'-, 2,3'-, dihydroxydiphenyl ethers, 4,4'-dihydroxy-3,6-dimethyldiphenyl ether, bis-(4-hydroxy-3-isobutylphenyl) ether, bis-(4-hydroxy-3-isopropylphenyl) ether, bis-(4-hydroxy-3-chlorophenyl) ether, bis-(4-hydroxy-3-fluorophenyl) ether, bis-(4-hydroxy-3-bromophenyl) ether, bis-(4-hydroxynapthyl) ether, bis-(4-hydroxy-3-chloronaphthyl) ether, bis-(2-hydroxydiphenyl) ether, 4,4'-dihydroxy-2,6-dimethoxydiphenyl ether, and 4,4'-dihydroxy-2,5-diethoxydiphenyl ether.

The preferred dihydric polynuclear phenols are represented by the formula:

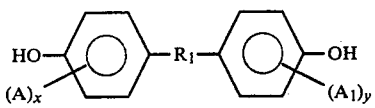

wherein A and A$_1$ are as previously defined, x and y have values from 0 to 4 inclusive and R$_1$ is a divalent saturated aliphatic hydrocarbon radical, particularly alkylene and alkylidene radicals having from 1 to 3 carbon atoms and cycloalkylene radicals having up to and including 10 carbon atoms. The most preferred dihydric phenol is bisphenol-A, i.e., 2,2-bis(p-hydroxyphenyl) propane.

The halo-epoxy alkane can be represented by the formula:

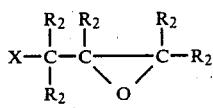

wherein X is a halogen atom (e.g., chlorine and bromine), each R$_2$ individually is hydrogen or alkyl group of up to 7 carbon atoms; wherein the number of carbon atoms in any epoxy alkyl group generally totals no more than 10 carbon atoms.

While glycidyl ethers, such as derived from epichlorohydrin, are particularly preferred, the epoxy polymers containing epoxy-alkoxy groups of a greater number of carbon atoms are also suitable. These are prepared by substituting for epichlorohydrin such representative corresponding chlorides or bromides of monohydroxy epoxyalkanes as 1-chloro-2,3-epoxybutane, 2-chloro-3,4-epoxybutane, 1-chloro-2-methyl-2,3-epoxypropane, 1-bromo-2,3-epoxypentane, 2-chloromethyl-1,2-epoxybutane, 1-bromo-4-ethyl-2,3-epoxypentane, 4-chloro-2-methyl-2,3-epoxypentane, 1-chloro-2,3-epoxyoctane, 1-chloro-2-methyl-2,3-epoxyoctane, or 1-chloro-2,3-epoxydecane.

The epoxidized novolaks can be represented by the formula:

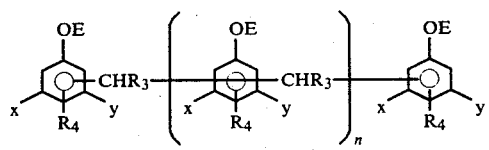

wherein n is at least about 0.2; E is hydrogen or an epoxyalkyl group, at least two E groups per polymer molecule being an epoxyalkyl group and wherein the epoxyalkyl group is represented by the formula:

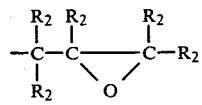

R$_3$ is hydrogen or alkyl or alkylene or aryl or aralkyl or alkaryl or cycloalkyl or furyl group; each R$_2$ individually is hydrogen or alkyl group of up to 7 carbon atoms; wherein the number of carbon atoms in any epoxyalkyl group totals no more than 10 carbon atoms; each X and Y is individually hydrogen or chlorine or alkyl or hydroxyl; each R$_4$ individually is hydrogen or chlorine or a hydrocarbon group. Preferably, substantially all of the E groups are epoxyalkyl groups. Generally R$_3$, X, Y, and R$_4$ when hydrocarbons, contain no more than about 12 carbon atoms.

The epoxy novolaks can be prepared by known methods by the reaction of a thermoplastic phenolic-aldehyde polymer of a phenol having the formula:

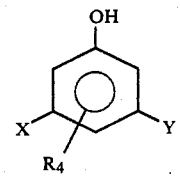

wherein X, Y, and R$_4$ have the meaning as defined above with a halo-epoxy alkane of the formula:

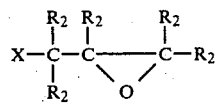

wherein X is a halogen atom (e.g., chlorine, bromine, and the like) and R$_2$ have the same meanings as defined hereinabove.

Hydrocarbon-substituted phenols having two available positions ortho or para to a phenolic hydroxy group for aldehyde condensation to provide polymers suitable for the preparation of epoxy novolaks include o- and p-cresols, o- and p-ethyl phenols, o- and p-isopropyl phenols, o- and p-sec-butyl phenols, o- and p-amyl phenols, o- and p-octyl phenols, o- and p-nonyl phenols, 2,5-xylenol, 3,4-xylenol, 2,5-diethyl phenol, 3,4-diethyl phenol, 2,5-diisopropyl phenol, 4-methyl resorcinol, 4-ethyl resorcinol, 4-isopropyl resorcinol, 4-tert-butyl resorcinol, o- and p-benzyl phenols, o- and p-phenethyl phenols, o- and p-phenyl phenols, o- and p-tolyl resorcinol, and 4-cyclohexyl resorcinol.

Various chloro-substituted phenols which can also be used in the preparation of phenol-aldehyde resins suitable for the preparation of the epoxy novolaks include o- and p-chloro-phenols, 2,5-dichloro phenol, 2,3-dichloro phenol, 3,4-dichloro phenol, 2-chloro-3-methyl phenol, 2-chloro-5-methyl-phenol, 3-chloro-2-methyl phenol, 5-chloro-2-methyl phenol, 3-chloro-4-ethyl phenol, 4-chloro-3-methyl phenol, 4-chloro-3-ethyl phenol, 4-chloro-3-isopropyl phenol, 3-chloro-4-phenyl phenol, 3-chloro-4-chlorophenyl phenols, 3,5-dichloro-4-methyl phenol, 3,5-dichloro-2-methyl phenol, 2,3-dichloro-5-methyl phenol, 2,5-dichloro-3-methyl phenol, 3-chloro-4,5-dimethyl phenol, 4-chloro-3,5-dimethyl phenol, 2-chloro-3,5-dimethyl phenol, 5-chloro-2,3-dimethyl phenol, 5-chloro-3,4-dimethyl phenol, 2,3,5-trichloro phenol, 3,4,5-trichloro phenol, 4-chloro resorcinol, 4,5-dichloro resorcinol, 4-chloro-5-methyl resorcinol, and 5-chloro-4-methyl resorcinol.

Typical phenols which have more than two positions ortho or para to a phenolic hydroxy group available for aldehyde condensation and which, by controlled aldehyde condensation, can also be used are: phenol, m-cresol, 3,5-xylenol, m-ethyl and m-isopropyl phenols, m,m'-diethyl and m,m'-diisopropyl phenols, m-butyl-phenols, m-amyl phenols, m-octyl phenols, m-nonyl phenols, resorcinol, 5-methyl-resorcinol, and 5-ethyl resorcinol.

As condensing agents any aldehyde may be used which will condense with the particular phenol being used, including formaldehyde, acetaldehyde, propionaldehyde, butyraldehyde, heptaldehyde, benzaldehyde, and alkyl-substituted benzaldehydes, such as toluic aldehyde; napthaldehyde, furfuraldehyde, glyoxal, acrolein, or compounds capable of engendering aldehydes such as para-formaldehyde and hexamethylene tetramine. The aldehydes can also be used in the form of a solution, such as the commercially available formalin.

While glycidyl ethers, such as derived from epichlorohydrin, are preferred, the epoxy novolak polymers can contain epoxy-alkoxy groups of a greater number of carbon atoms. These are prepared by substituting for epichlorohydrin such representative corresponding chlorides or bromides of monohydroxy epoxyalkanes as 1-chloro-2, 3-epoxybutane, 2-chloro-3, 4-epoxybutane, 1-chloro-2-methyl-2, 3-epoxypropane, 1-bromo-2, 3-epoxypentane, 2-chloromethyl-1, 2-epoxybutane, 1-bromo-4-ethyl-2, 3-epoxypentane, 4-chloro-2-methyl-2, 3-epoxypentane, 1-chloro-2, 3-epoxyoctane, 1-chloro-2-methyl-2, 3-epoxyoctane, or 1-chloro-2, 3-epoxydecane.

Preferred epoxidized novolaks are represented by the formula:

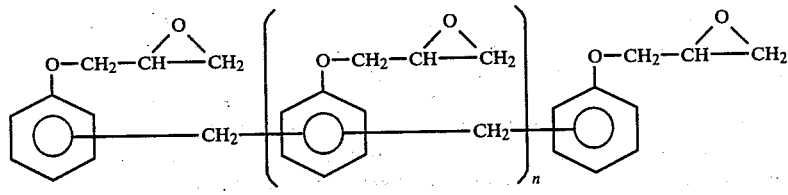

wherein n is at least about 0.2. The epoxidized novolak preferably is liquid and preferably n is less than about 1.5.

Examples of reaction products of glycidyl ethers with polymers terminated with reactive groups include reaction products of glycidyl ether of bisphenol-A and epichlorohydrin with telechelic prepolymers (i.e., prepolymers having the reactive groups capable of producing strong elastomeric structures). The prepolymers are usually liquids. Examples of some polymer chains include polysulfide, polyisobutylene; polybutadiene, butadiene-acrylonitrile copolymer, polyamide, polyether and polyester. The reactive terminal groups include thiol, carboxyl, hydroxyl, amine, and isocyanate. A preferred telechelic prepolymer is carboxyl terminated butadiene-acrylonitrile prepolymer. Also, suitable epoxy polymers include epoxidized unsaturated oils such as epoxidized linseed and soybean oil. Such preferably have an oxirane content of about 7 to about 8% by weight.

When the polymeric cyclopentadiene derivatives are employed in admixture with other materials of the type discussed above as auxiliary binders, such as furfuryl alcohol and/or disubstituted cyclopentadiene derivatives, and/or fulvenes, and/or furan polymers and/or phenolics and/or epoxy polymers, such polymeric cyclopentadiene derivatives are generally employed in amounts of about 90 to about 50% by weight based upon the total amount of polymeric cyclopentadiene derivative and other materials defined above.

In addition, the compositions can contain a dialkyl ester of the formula:

wherein each $R_1$ and $R_2$ individually is an alkyl of 1 to 20 carbon atoms and n is a whole number integer of 0 to 4. The ester may be blended with the binder and/or sand and/or in conjunction with the acidic catalyst. Suitable esters include dimethyl oxalate, diethyl oxalate, dimethyl succinate, methyl-ethyl succinate, methyl-n-propyl succinate, methyl isopropyl succinate, methyl-n-butyl succinate, diethyl succinate, ethyl-n-propyl succinate, diisopropyl succinate, dibutyl succinate, dimethyl glutarate, methylethyl glutarate, methyl-n-butyl glutarate, methyl-isobutyl glutarate, diethyl glutarate, ethyl-n-propyl glutarate, diisopropyl glutarate, dibutyl glutarate, dimethyl adipate, methylethyl adipate, methyl-n-propyl adipate, methylisopropyl adipate, diethyl adipate, dipropyl adipate, dibutyl adipate, dioctyl succinate, dioctyl adipate, octyl-nonyl glutarate, diheptyl glutarate, didecyl adipate, dicapryl adipate, dicapryl succinate, dicapryl glutarate, dilauryl adipate, dilauryl succinate, dilauryl glutarate and malonic acid esters.

Preferred esters for use are the oxalates; dimethyl glutarate such as available from DuPont under the trade designation DBE-5; dimethyl adipate available from DuPont under the trade designation DBE-6; and mixtures of such esters such as are available from DuPont under the trade designation DBE. Other diluents can be employed if desired and include such groups of compounds as ketones such as acetone, methylethyl ketone and diisoamylketone; ketoacid esters such as ethyl acetoacetate and methyl acetoacetate; and other esters such as the cellosolve esters.

The diluent may generally be employed in an amount of from about 0.5 to 30% and preferably 1.0 to 10% by weight of the binder.

When preparing an ordinary sand-type foundry shape, the aggregate employed has a particle size large enough to permit sufficient porosity in the foundry shape to permit escape of volatiles from the shape during the casting operation. The term "ordinary sand-type foundry shapes" as used herein refers to foundry shapes which have sufficient porosity to permit escape of volatiles from it during the casting operation. Generally, at least about 80%, and preferably about 90%, by weight of aggregate employed for foundry shapes has an average particle size no smaller than about 150 mesh (Tyler screen mesh). The aggregate for foundry shapes preferably has an average particle size between about 50 and about 150 mesh (Tyler screen mesh). The preferred aggregate employed for ordinary foundry shapes is silica sand wherein at least about 70 weight percent, and preferably at least about 85 weight percent of the sand is silica. Other suitable aggregate materials include zircon, olivine, aluminosilicate sand, chromite sand and the like.

When preparing a shape for precision casting, the predominant portion, and generally at least about 80% of the aggregate, has an average particle size no larger than about 150 mesh (Tyler screen mesh). Preferably at least about 90% by weight of the aggregate for precision casting applications has a particle size no larger than 150 mesh and preferably between 325 mesh and 200 mesh. The preferred aggregates employed for precision casting applications are fused quartz, zircon sands, magnesium silicate sands such as olivine, and aluminosilicate sands.

Shapes for precision casting differ from ordinary sand-type foundry shapes in that the aggregate in shapes for precision casting can be more densely packed than the aggregate in shapes for ordinary sand-type foundry shapes. Therefore, shapes for precision casting must be heated before being utilized to drive off volatizable material present in the molding composition. If the volatiles are not removed from a precision casting shape before use, vapor created during casting will diffuse into the molten melt, since the shape has a relatively low porosity. The vapor diffusion would decrease the smoothness of the surface of the precision cast article.

When preparing a refractory, such as a ceramic, the predominant portion and at least about 80% by weight of the aggregate employed has an average particle size under 200 mesh and preferably no larger than 325 mesh. Preferably at least about 90% by weight of the aggregate for a refractory has an average particle size under 200 mesh, and preferably no larger than 325 mesh. The aggregate employed in the preparation of refractories must be capable of withstanding the curing temperatures, such as above about 1500° F. which are needed to cause sintering for utilization.

Examples of some suitable aggregate employed for preparing refractories include the ceramics, such as refractory oxides, carbides, nitrides, and silicides, such as aluminum oxide, lead oxide, chromic oxide, zirconium oxide, silica, silicon carbide, titanium nitride, boron nitride, molybdenum disilicide, and carbonaceous material, such as graphite. Mixtures of the aggregates can also be used, when desired, including mixtures of metals and the ceramics.

Examples of some abrasive grains for preparing abrasive articles include aluminum oxide, silicon carbide, boron carbide, corundum, garnet, emery and mixtures thereof. The grit size is of the usual grades as graded by the United States Bureau of Standards. These abrasive materials and their uses for particular jobs are understood by persons skilled in the art and are not altered in the abrasive articles contemplated by the present invention. In addition, inorganic filler can be employed along with the abrasive grit in preparing abrasive articles. It is preferred that at least about 85% of the inorganic fillers has an average particle size no greater than 200 mesh. It is most preferred that at least about 95% of the inorganic filler has an average particle size no greater than 200 mesh. Some inorganic fillers include cryolite, fluorospar, silica and the like. When an organic filler is employed along with the abrasive grit, it is generally present in amounts from about 1 to about 30% by weight based upon the combined weight of the abrasive grit and inorganic filler.

In molding compositions, the aggregate constitutes the major constituent and the binder constitutes a relatively minor amount. In ordinary sand type foundry applications, the amount of binder is generally no greater than about 10% by weight and frequently within the range of about 0.5 to about 7% by weight based upon the weight of the aggregate. Most often, the binder content ranges from about 0.6 to about 5% by weight based upon the weight of the aggregate in ordinary sand type foundry shapes.

In molds and cores for precision casting application the amount of binder is generally no greater than about 40% by weight and frequently within the range of about 5 to about 20% by weight based upon the weight of the aggregate.

In refractories, the amount of binder is generally no greater than about 40% by weight and frequently within the range of about 5% to about 20% by weight based upon the weight of the aggregate.

In abrasive articles, the amount of binder is generally no greater than about 25% by weight and frequently within the range of about 5% to about 15% by weight based upon the weight of the abrasive material or grit.

A valuable additive to the binder compositions of the present invention in certain types of sand is a silane having the general formula:

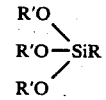

wherein R' is a hydrocarbon radical and preferably an alkyl radical of 1 to 6 carbon atoms and R is a hydrocarbon group such as a vinyl group or an alkyl radical; an alkoxy-substituted alkyl radical; or an alkyl-aminesubstituted alkyl radical in which the alkyl groups have from 1 to 6 carbon atoms. The aforesaid silane when employed in concentrations of about 0.05 to 2% based on the binder component of the composition improves the humidity resistance of the system.

Examples of some commercially available silanes are Dow Corning Z6040; Union Carbide A187 (gamma glycidoxy propyltrimethoxy silane); Union Carbide A1100 (gamma amino-propyltriethoxy silane); Union Carbide A1120 [N-beta-(amino-ethyl)-gamma aminopropyltrimethoxy silane]; vinyltriethoxysilane; and Union Carbide A186 (beta-3,4-epoxy-cyclohexyl)-ethyltrimethoxysilane.

When the compositions of the present invention are used to prepare ordinary sand-type foundry shapes, the following steps are employed:
1. Forming a foundry mix containing an aggregate (e.g., sand) and the bonding agent;
2. Introducing the foundry mix into a mold or pattern to thereby form the desired shape;
3. Allowing the shape to obtain a minimum strength in the mold; and
4. Thereafter removing the shape from the mold or pattern allowing it to further cure thereby obtaining a hard solid cured foundry shape.

The foundry mix can optionally contain other ingredients such as iron oxide, ground flax fibers, wood cereals, pitch, refractory flours, and the like.

The systems of the present invention can be used for the casting of the relatively high melting point ferrous-type metals such as iron and steel which are poured at about 2500° F., as well as for the casting of the relatively low melting point nonferrous type metals such as aluminum, copper, and copper alloys including brass.

In order to further understand the present invention, the following non-limiting examples concerned with foundry are provided. All parts are by weight unless the contrary is stated. The foundry samples are cured by the so-called "no-bake" process.

Examples 1 to 8 represent preparations of polymeric cyclopentadiene derivatives of the present invention:

EXAMPLE 1

Into a 3-neck flask equipped with a stirrer, condenser, thermometer and $N_2$-inlet are added about 112 grams of KOH dissolved in about 250 ml of isopropanol and 150 ml of methanol. At room temperature, about 347 grams (about 5.25 moles) of freshly distilled cyclopentadiene, which is kept at the temperature of dry ice/acetone, are added and the mixture is allowed to warm up to about 20° C. Next, 570 grams (about 5 moles) of methylamylketone are added at a rate of about 35 ml/minute. The reaction is exothermic and the temperature increases to about 70° C. After the addition is completed, the temperature is held at about 70° C. for about 75 minutes. Then about 1.25 moles of formaldehyde at a 55% solution in a mixture of 92% methanol and 8% water are added over a period of about 10 minutes. The temperature increases to about 78° C. and reflux can be observed. When all of the formaldehyde is added, the temperature is held at about 75° C. for about 2 hours. Then about 319 grams of acetone are added at a rate of about 35 ml/min. and the mixture is allowed to react at 67°–70° C. for another 20 hours. The mixture is then neutralized with 10% HCl under cooling and the layers are separated. The organic phase is then evaporated at 10–15 mm Hg/50° C. and is then filtered.

The product has a viscosity at 25° C. of about 306 cps and a refractive index at 25° C. of about 1.5484. No free formaldehyde is detected. The average molecular weights are: $M_w=347$, $M_n=225$ (by GPC analysis).

EXAMPLE 2

Example 1 is repeated except that 2.5 moles formaldehyde are added over a period of 20 minutes. The product has a viscosity at 25° C. of about 910 cps and a refractive index at 25° C. of about 1.5520. No free formaldehyde is detected. The average molecular weights are $M_w=604$, $M_n=282$ (by GPC analysis).

EXAMPLE 3

Example 1 is repeated except that 3.75 moles formaldehyde are added over a period of 30 min. The product has a viscosity at 25° C. of about 24 stokes and a refractive index at 25° C. of about 1.5511. No free formaldehyde is detected. The average molecular weights are $M_w=891$, $M_n=327$ (by GPC analysis).

EXAMPLE 4

Example 3 is repeated except that there is no reaction with acetone. The product has a viscosity at 25° C. of about 16.6 stokes and a refractive index at 25° C. of about 1.5402. No free formaldehyde is detected. The average molecular weights are $M_w=809$, $M_n=324$ (by GPC analysis).

EXAMPLE 5

Example 4 is repeated except that 501 g methylisobutylketone are employed in place of methylamylketone. The product has a viscosity at 25° C. of about 41 stokes and a refractive index at 25° C. of about 1.5255. No free formaldehyde is detected. The average molecular weights are $M_w=1525$, $M_n=279$ (by GPC analysis).

EXAMPLE 6

Example 5 is repeated except that the formaldehyde is added at 50° C. over a period of 1.5 hrs. After it has reacted for two more hours, 640 g acetone are added at a rate of 100 ml/min. and the mixture is allowed to react for 6 hrs. at 60° C. The excess acetone is distilled off before neutralization. The product has a viscosity at 25° C. of about 539 cps and a refractive index at 25° C. of about 1.5500. No free formaldehyde is detected. The average molecular weights are $M_w=479$, $M_n=235$ (by GPC analysis).

EXAMPLE 7

Example 6 is repeated except that 23.5 g phenol are added to the mixture prior to the addition of 4.5 moles formaldehyde at 50° C. over a period of 2.5 hrs. The product has a viscosity at 25° C. of about 175 cps and a refractive index at 25° C. of about 1.5347. No free formaldehyde is detected. The average molecular weights are $M_w=620$, $M_n=226$ (by GPC analysis).

EXAMPLE 8

Example 1 is repeated except that a disubstituted cyclopentadiene prepared according to Example 2 of application Ser. No. 300,786 is reacted with formaldehyde. The formaldehyde is added over a period of about 40 minutes under cooling between about 24° C. and about 40° C. The mixture is then allowed to react for 2 additional hours. The product has a viscosity at 25° C. of about 120 stokes and a refractive index at 25° C. of about 1.5575. No free formaldehyde is detected.

EXAMPLES 9–16

Foundry sand mixes are prepared by admixing sand with the binder compositions shown in Tables 1 and 2 below. The resulting foundry sand mixes are then formed into standard AFS tensile test samples using the standard procedures. The cured samples are tested for tensile strength and hardness.

TABLE 1

| EXAMPLES 9–16 - COMPOSITION AND TENSILE STRENGTHS | | | | | | | | | |
|---|---|---|---|---|---|---|---|---|---|
| (A) | Substituted Cyclopentadiene Polymers | | | | | | | | |
| | Polymer prepared according to Example 1 | 64.4 | | | | | | | |
| | Polymer prepared according to Example 2 | | 64.4 | | | | | | |
| | Polymer prepared according to Example 3 | | | 64.4 | | | | | |
| | Polymer prepared according to Example 4 | | | | 64.4 | | | | |
| | Polymer prepared according to Example 5 | | | | | 64.4 | | | |
| | Polymer prepared according to Example 6 | | | | | | 64.4 | | |
| | Polymer prepared according to Example 7 | | | | | | | 64.4 | |
| | Polymer prepared according to Example 8 | | | | | | | | 64.4 |
| (B) | Epoxy Resin Epon 828 (Shell) | 27.6 | 27.6 | 27.6 | 27.6 | 27.6 | 27.6 | 27.6 | 27.6 |
| (C) | DBE-2 (DuPont) | 4.4 | 4.4 | 4.4 | 4.4 | 4.4 | 4.4 | 4.4 | 4.4 |
| (D) | TXIB (Kodak) | 2.7 | 2.7 | 2.7 | 2.7 | 2.7 | 2.7 | 2.7 | 2.7 |
| (E) | BHT (ppm) | 500 | 500 | 500 | 500 | 500 | 500 | 500 | 500 |
| (F) | Silane A-186 | 0.9 | 0.9 | 0.9 | 0.9 | 0.9 | 0.9 | 0.9 | 0.9 |

TABLE 1-continued

EXAMPLES 9-16 - COMPOSITION AND TENSILE STRENGTHS

| (G) | BF$_3$.2H$_2$O catalyst (% based on binder) | | | | | | | | |
|---|---|---|---|---|---|---|---|---|---|
| | 17.5% BF$_3$.2H$_2$O/41.25% Glycerine/41.25% PeP 450 | 8.2 | 8.2 | 8.2 | | | | | 6.8 |
| | 15% BF$_3$.2H$_2$O/42.5% Glycerine/42.5% PeP 450 | | | | 6.8 | 6.8 | 6.8 | 8.2 | |
| Work Time/Strip Time | | 28/49 | 27/55 | 29/55 | 27/67 | 39/84 | 41/85 | 23/40 | 25/46 |
| Tensiles (PSI) | | | | | | | | | |
| 1 Hr. | | 258 | 275 | 250 | 90 | 65 | 93 | 122 | 108 |
| 3 Hrs. | | 338 | 378 | 337 | 140 | 178 | 162 | 158 | 115 |
| 24 Hrs. | | 343 | 375 | 362 | 258 | 185 | 187 | 253 | 118 |

"Pep 450" is available from BASF and is a tetrol of about 400 molecular weight obtained from reacting pentaerythritol with propylene oxide.

EXAMPLE 17

Part A

Erosion wedge cores are prepared using the compositions and curing techniques of Examples 10 and 11 hereinabove. The cores are used to have poured therein gray iron at 2700° F. Only slight to moderate erosion is observed.

Companion Part B

Part A of Example 17 is repeated except that the binder contains the disubstituted cyclopentadiene prepared according to Example 2 of application Ser. No. 300,786 instead of the polymers of Examples 10 and 11. Severe erosion is observed.

What is claimed is:

1. Polymeric cyclopentadiene derivative having recurring units of the formula I or isomers thereof or mixtures thereof:

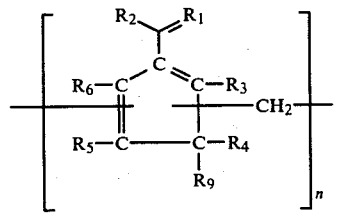

wherein each $R_1$ and $R_2$ individually is a hydrocarbon containing 1 to 10 carbon atoms, or a hydrocarbon containing one or more oxygen bridges, or a furyl group; or are interconnected and together with the carbon atom to which they are connected form a cycloaliphatic hydrocarbon group, or one of $R_1$ or $R_2$ is hydrogen; each $R_3$, $R_4$, $R_5$, $R_6$, and $R_9$ is individually hydrogen, methyl, —CH$_2$—, or

provided that two of $R_3$, $R_5$, $R_6$, and $R_4$ or $R_9$ are —CH$_2$— and that at least two of said $R_3$, $R_4$, $R_5$, $R_6$, and $R_9$ are hydrogen; and wherein each $R_7$ and $R_8$ individually is a hydrocarbon group containing 1 to 10 carbon atoms, or a hydrocarbon group containing one or more oxygen bridges, or are interconnected and together with the carbon atoms to which they are connected form a cycloaliphatic hydrogen group, or one of $R_7$ or $R_8$ is hydrogen, or $R_4$ or $R_5$ or $R_9$ is:

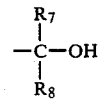

and wherein n is at least 2.

2. The derivative of claim 1 wherein at least one of $R_1$ and $R_2$ is methyl and the other is an alkyl of 2 to 5 carbon atoms.

3. The derivative of claim 1 wherein three of $R_3$, $R_4$, $R_5$, $R_6$, and $R_9$ are H.

4. The derivative of claim 1 wherein $R_1$ is methyl and $R_2$ is isobutyl.

5. The derivative of claim 1 wherein $R_1$ and $R_2$ are interconnected and form a cyclohexyl ring with the common carbon atom to which they are attached.

6. The derivative of claim 1 wherein $R_1$ is methyl and $R_2$ is ethyl.

7. The derivative of claim 1 wherein $R_1$ and $R_2$ are phenyl.

8. The derivative of claim 1 wherein $R_1$ is furyl and $R_2$ is H.

9. The derivative of claim 1 wherein $R_1$ and $R_2$ are isobutyl.

10. The derivative of claim 1 wherein $R_1$ and $R_2$ are interconnected and form an isophoronefulvene ring with the common carbon atom to which they are connected.

11. The derivative of claim 1 wherein n is an integer of about 2 to about 9.

12. The derivative of claim 1 having a molecular weight of about 350 to about 1525.

13. A composition containing at least one polymeric cyclopentadiene derivative having recurring units of the formula I or isomers thereof or mixtures thereof:

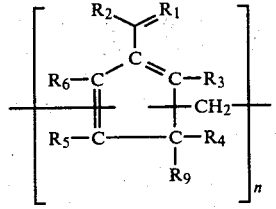

wherein each $R_1$ and $R_2$ individually is a hydrocarbon containing 1 to 10 carbon atoms or a hydrocarbon containing one or more oxygen bridges in the chain and containing up to 10 carbon atoms, or a furyl group; or are interconnected and together with the carbon atom to which they are connected form a cycloaliphatic hydrocarbon group or one of $R_1$ or $R_2$ is hydrogen and wherein each $R_3$, $R_4$, $R_5$, $R_6$, and $R_9$ individually is hydrogen or —CH$_2$— or methyl or or $R_4$ or $R_9$ or $R_5$ is

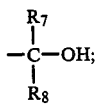

wherein each $R_7$ and $R_8$ individually is a hydrocarbon group containing 1–10 carbon atoms, or a hydrocarbon containing one or more oxygen bridges in the chain and containing up to 10 carbon atoms or are interconnected and together with the carbon atom to which they are connected form a cycloaliphatic hydrocarbon group; or one of $R_7$ or $R_8$ is hydrogen, and provided that at least two of $R_3$, $R_5$, $R_6$, and $R_4$ or $R_9$ are —$CH_2$— and that at least two of said $R_3$, $R_4$, $R_5$, $R_6$, and $R_9$ are hydrogen; and wherein n is at least 2; and an effective catalytic amount of an acidic catalyst having a pka of about 4 or less.

14. The composition of claim 13 wherein at least one of $R_1$ and $R_2$ is methyl and the other is an alkyl of 2 to 5 carbon atoms.

15. The composition of claim 13 wherein three of $R_3$, $R_4$, $R_5$, $R_6$, and $R_9$ are H.

16. The composition of claim 15 wherein $R_1$ is methyl and $R_2$ is isobutyl.

17. The composition of claim 15 wherein $R_1$ and $R_2$ are interconnected and form a cyclohexyl ring with the common carbon atom to which they are attached.

18. The composition of claim 15 wherein $R_1$ is methyl and $R_2$ is ethyl.

19. The composition of claim 15 wherein $R_1$ and $R_2$ are phenyl.

20. The composition of claim 15 wherein $R_1$ is furyl and $R_2$ is H.

21. The composition of claim 15 wherein $R_1$ and $R_2$ are isobutyl.

22. The composition of claim 15 wherein $R_1$ and $R_2$ are interconnected and form an isophoronefulvene ring with the common carbon atom to which they are connected.

23. The composition of claim 13 wherein n is an integer of about 2 to about 9.

24. The composition of claim 13 wherein said derivative has a molecular weight of about 350 to about 1525.

25. The composition of claim 13 wherein the amount of said acidic catalyst is at least about 0.8% by weight.

26. The composition of claim 13 wherein said catalyst is a Lewis Acid.

27. The composition of claim 26 wherein said Lewis Acid is $BF_3$.

28. A molding composition which comprises a major amount of aggregate and an effective bonding amount up to about 40% by weight of the aggregate of the composition of claim 13.

29. The molding composition of claim 28 which is a foundry composition containing up to about 10% by weight of the aggregate of said composition.

30. A process for the fabrication of molded articles which comprises:

(a) mixing the aggregate with a bonding amount up to about 40% by weight based upon the weight of the aggregate of a composition of claim 13;
(b) introducing the composition obtained from step (a) into a pattern;
(c) hardening the composition in the pattern to become self-supporting; and
(d) thereafter removing the shaped article of step (c) from the pattern and allowing it to further cure, thereby obtaining a hardened, solid, cured, molded article.

31. A process for the fabrication of molded articles which comprises:

(a) mixing the aggregate with a bonding amount of to about 40% by weight based upon the weight of the aggregate of at least one derivative of claim 1;
(b) introducing the composition obtained from step (a) into a pattern;
(c) hardening the composition in the pattern to become self-supporting by passing an acidic gas through the composition; and
(d) thereafter removing the shaped article of step (c) from the pattern and allowing it to further cure, thereby obtaining a hardened, solid, cured, molded article.

32. A process for preparing polymeric cyclopentadiene derivative which comprises reacting cyclopentadiene derivative having the formula:

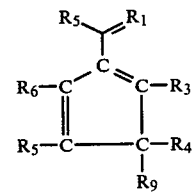

isomers, or mixtures thereof; wherein each $R_1$ and $R_2$ individually is a hydrocarbon containing 1 to 10 carbon atoms or a hydrocarbon containing one or more oxygen bridges in the chain and contains up to 10 carbon atoms; or are interconnected and together with the carbon atom to which they are connected form a cycloaliphatic hydrocarbon group or one of $R_1$ or $R_2$ is hydrogen; each $R_3$, $R_4$, $R_5$, $R_6$, and $R_9$ individually is hydrogen, methyl, or

or $R_4$ or $R_9$ or $R_5$ is

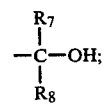

wherein each $R_7$ and $R_8$ individually is a hydrocarbon containing 1 to 10 carbon atoms or a hydrocarbon containing one or more oxygen bridges in the chain and containing up to 10 carbon atoms; or are interconnected and together with the carbon atom to which they are connected form a cycloaliphatic hydrocarbon group or furyl or one of $R_7$ or $R_8$ is hydrogen, and provided that at least four of $R_3$, $R_4$, $R_5$, $R_6$, and $R_9$ are hydrogen; with formaldehyde in the presence of a basic catalyst to provide a polymeric cyclopentadiene derivative;

wherein about 0.1 to about 1 mole of formaldehyde per mole of said cyclopentadiene derivative is employed.

33. The process of claim 32 wherein about 0.25 to about 0.75 moles of formaldehyde per mole of said cyclopentadiene derivative are employed.

34. A polymeric cyclopentadiene derivative obtained by the process of claim 32.

35. The process of claim 32 wherein said basic catalyst is selected from the group of strong bases, amines and basic ion exchange resins.

36. The process of claim 32 wherein the reaction is carried out at temperatures of about 60°–90° C. in about 5 to about 25 hours.

* * * * *